(12) United States Patent
Kranbuehl

(10) Patent No.: US 9,897,586 B2
(45) Date of Patent: Feb. 20, 2018

(54) MULTI POINT METHOD AND APPARATUS FOR MONITORING THE AGING AND CHANGES IN CORRESPONDING TENSILE PERFORMANCE PROPERTIES OF A POLYMER

(71) Applicant: David Kranbuehl, Williamsburg, VA (US)

(72) Inventor: David Kranbuehl, Williamsburg, VA (US)

( * ) Notice: Subject to any disclaimer, the term of this patent is extended or adjusted under 35 U.S.C. 154(b) by 402 days.

(21) Appl. No.: 14/295,675

(22) Filed: Jun. 4, 2014

(65) Prior Publication Data

US 2016/0003796 A1 Jan. 7, 2016

Related U.S. Application Data

(60) Provisional application No. 61/831,179, filed on Jun. 5, 2013.

(51) Int. Cl.
*G01N 33/44* (2006.01)
*G01N 30/88* (2006.01)
*G01N 17/04* (2006.01)
*G01N 3/08* (2006.01)
G01N 30/74 (2006.01)

(52) U.S. Cl.
CPC ............. *G01N 33/442* (2013.01); *G01N 3/08* (2013.01); *G01N 17/043* (2013.01); *G01N 30/88* (2013.01); *G01N 30/74* (2013.01); *G01N 2030/885* (2013.01)

(58) Field of Classification Search
CPC .......................... G01N 33/442; G01N 17/043
See application file for complete search history.

(56) References Cited

U.S. PATENT DOCUMENTS

| | | | | |
|---|---|---|---|---|
| 5,614,683 A | * | 3/1997 | Kranbuehl | G01N 33/442 73/866 |
| 7,069,772 B2 | | 7/2006 | Kranbuehl | |
| 7,487,666 B2 | * | 2/2009 | Kranbuehl | G01N 17/00 73/86 |
| 2016/0187315 A1 | * | 6/2016 | Blumenfeld | G01N 33/2882 506/4 |

* cited by examiner

*Primary Examiner* — Ryan Walsh
(74) *Attorney, Agent, or Firm* — Whitham, Curtis & Cook, P.C.

(57) ABSTRACT

The molecular weight distribution in a polymer sample can be used as a measure for when parts need to be replaced, and can be tracked over time to allow for predicting when parts need to be replaced and/or identifying the type of aging taking place in the polymer part. Molecular weight distribution determination has particular application in determining the replacement time and or aging parameters in polyamide (e.g., formed from 11-aminoundecanoic acid or formed from 12 aminododecanoic acid) polyvinyldiflouride, and polyethyelene pipe liners used in, for example, offshore oil and gas production and fuel transport operations.

5 Claims, 8 Drawing Sheets

MULTI POINT METHOD AND APPARATUS FOR MONITORING THE AGING AND CHANGES IN CORRESPONDING TENSILE PERFORMANCE PROPERTIES OF A POLYMER

CROSS-REFERENCE TO RELATED APPLICATIONS

This application claims priority to U.S. Provisional Application 61/831,179 filed Jun. 5, 2013. The complete contents thereof are herein incorporated by reference.

BACKGROUND

In U.S. Pat. No. 5,614,683 to Kranbuehl, which is herein incorporated by reference, it was demonstrated that average molecular weight was an important indicator of the life expectancy of a Nylon 11 (polyamide formed from 11-aminoundecanoic acid). In particular, the patent demonstrated that average molecular weight measurements correlated with elongation measurements for the aged polyamide, and that one could use the molecular weight measurement to identify when polyamide parts needed to be replaced.

Life monitoring of plastic and composite parts continues to grow in importance in modern industrial processes. As plastic materials replace metal materials in load bearing applications as well as in extreme and corrosive environments, there is a continuing need for improved methods to ascertain when a part should be replaced. Replacing after a pre-set period of time runs the dual risks of (1) waiting too long replace the part—i.e., in some situations the aging may occur earlier than the pre-set period, and (2) replacing the part too early—i.e., the part could have considerable life left even after the pre-set period expires.

SUMMARY

It has been determined that, while an average molecular weight can provide a person (or automated system) with information useful in determining whether it is time to replace a plastic part (see, e.g., U.S. Pat. No. 5,614,683 to Kranbuehl), a more accurate measure can be obtained by using a mass fraction analysis. That is, the critical feature for elasticity in a polymer (as measured by, for example, percent elongation at break) is the chain length of the polymer. All polymers are mixtures of polymer chains having varying chain lengths. With good manufacturing practices, the chain lengths in the polymer will generally fall with within a certain range. The molecular weight of a polymer correlates directly to its length (i.e., the longer the chain the greater the molecular weight). Thus, determining the mass fraction, i.e., molecular weight distribution for polymer chains in a polymer sample, a measure of the percentage of polymer chains that are longer than a critical length, can be obtained. The elasticity of the polymer is related to chain length (among other factors). For example, the longer the chain, the more chances for entanglements, etc. When the chain length (and hence molecular weight) deteriorates by oxidation, hydrolysis, scission, and other means, to a critical level, there is a sharp drop in elongation at break.

In one embodiment, the invention provides a methodology to determine when polymer parts should be replaced. In a particular application of the invention, the plastic part may be a polyamide (e.g., a polyamide formed from 11 aminoundecanoic acid (PA-11) or formed from 12 aminododecanoic acid (PA-12)) or polyethylene (PE) or polyvinylifluoride (PVDF) pipe liner used in off shore Oil and Gas production applications, i.e., plastic tubular liners which line the inside of a flexible metal pipe which extends from the sea floor to the oil and gas production vessel. However, it will be recognized that the applications can vary tremendously (e.g, the wings or fuselage of aircraft; the hull of a boat; auto parts, load bearing plastic beams, etc.). For example, in addition to PE and PVDF, the invention would be applicable to determining a replacement time for parts made of other vinyl addition polymers such as polystryene, polyproprylene, and polyvinylchloride, etc. The invention would be applicable for use in monitoring other polyamide parts as well as polyester parts for replacement. In one embodiment of the invention the molecular weight distribution for polymer chains in a polymer sample is determined, and from the molecular weight distribution, a fraction of polymer chains above a threshold value is determined. From this information, it can be determined whether a part is in need of replacement (for example, when a certain fraction is less than a preset value).

The invention also has applications in life monitoring of polymer parts. For example, witness coupons made of the same polymer as the polymer or composite part being monitored can be distributed at one or more locations on the part (e.g., up and down the length of a drilling pipe liner). These coupons will experience the same, in use, degradative effects experienced by the plastic part over time. By periodically retrieving the witness coupons and determining a molecular weight distribution for polymer chains in the witness coupons, one can get a molecular weight distribution value over time. By monitoring the molecular weight distribution at first, second, third, etc. (up to any number of time points), aging of the polymeric part can be evaluated. For example, by monitoring changes in molecular weight distribution over time, one can predict when a part will need to be replaced. This information may be used to schedule production or delivery of a replacement part prior to the part reaching a unusable state. As another example, by monitoring changes in the molecular weight distribution over time, one can determine whether the breakdown of the chain is due to, for example, oxidation (which is not desired in a pipe liner application, such as a drilling pipe liner) or hydrolysis (which is the desired breakdown pathway in a drilling pipe liner application). This information will allow the oil and gas operator to make adjustments to how, for example, the well is being operated to extend the life of the pipe liner part. This life monitoring technique can be used for monitoring polyamides and polyesters, as well as vinyl addition polymers such as PE, PVDF, polystyrene, polypropylene, polyvinylchloride, as well as other polymeric materials.

DETAILED DESCRIPTION

Figure 1:
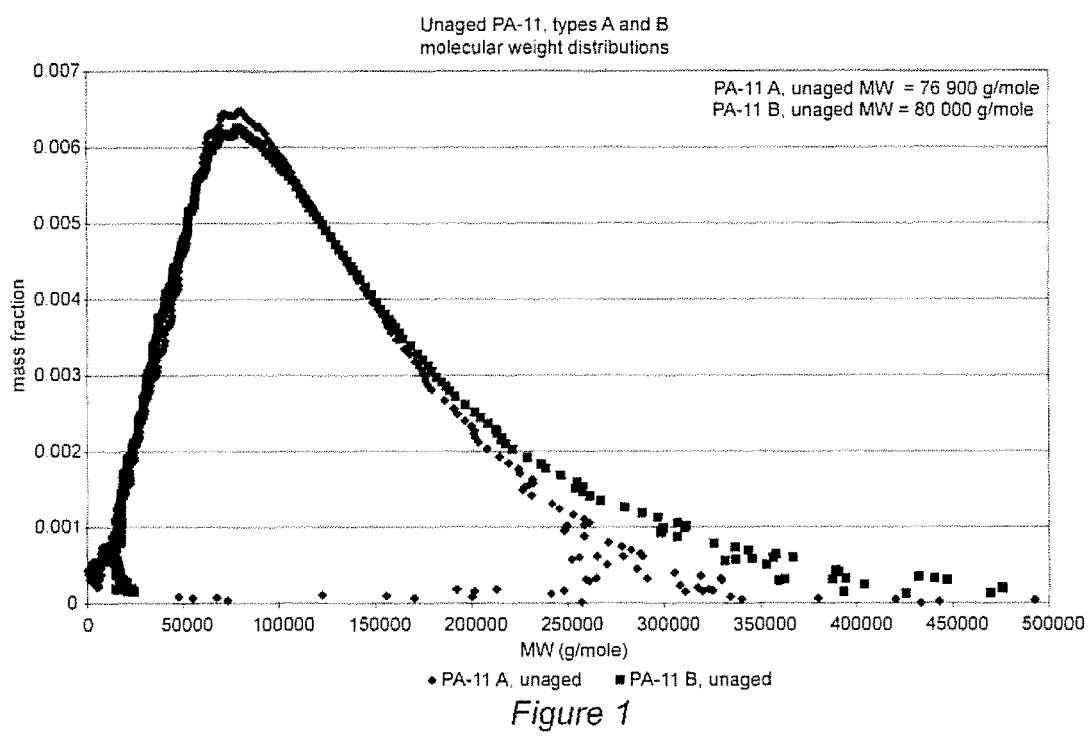
FIG. 1 shows a plot of molecular weight distributions in two types of unaged polyamide materials commonly used as the liner of a pipe.

Knowledge of the changes with age of the performance properties of a polymer, such as polyamides when used as the liner of a flexible pipe used to transport gas or crude oil, is critical for safe use and for cost effective planning of time for replacement. Of particular importance in many applications are the changes in the tensile properties, particularly percent (%) elongation at break, modulus, and maximum load. In previous work (see U.S. Pat. No. 5,614,683, U.S. Pat. No. 7,069,772, and U.S. Pat. No. 7,487,666, each of which is herein incorporated by reference) it has been shown that measuring the molecular weight of small witness coupon samples of the polymer in the use environment through primary molecular weight methods such as multi angle light scattering and indirect methods such as viscosity or size exclusion chromatography can be correlated with the changes in the required performance properties, such as elongation at break.

Here I propose a method which involves acquiring a detailed description of the mass fraction of polymer at each molecular weight and using this multi point information to correlate with the changing magnitude of the desired performance properties. The method can be practiced in a number of different applications. For example, polyamide pipes are used to transport crude in off shore applications, for the gasoline hoses used with automobiles, for the yellow natural gas lines used in suburban neighborhoods, and in other applications. This method can be employed in all of these environments, as well as in any other environments where monitoring polymeric parts, such as flexible polymeric pipe liners, would be an advantage.

This is a more informative, more sensitive and more accurate means to determine changes in performance properties such as tensile properties. Properties such as elasticity as measured by % elongation at break, are a function of entanglements between the polymer chains. When a chain becomes shorter than a critical length, there is a sharp drop in the % elongation at break as there are far fewer and much easier entanglements to pull apart due to falling below a critical length. Measurement of the average chain length is a means to detect this ductile to brittle transition as the polymers' lengths decrease during use from chemical scission of the chains due to oxidation or hydrolysis as examples of chemical aging. But there is always a distribution in the lengths of the chains produced in typical polymer fabrication processes. Thus, some of the chains will be longer than the critical length for entanglement and some shorter. What determines the elasticity and many other desired performance properties is the mass fraction of the polymer that is above this critical entanglement value. One can have various amounts of material above the critical length and still have the same average molecular weight. And there can be the same elasticity and fraction of the mass above the critical molecular weight with polymers having different molecular weight averages. As demonstrated herein, this is a function of the shape of the mass molecular weight/length distribution. Hence, the use of an average length as measured by an average of the molecular weights is a method with a lot of scatter in correlating molecular weight to a performance property such as % elongation at break. By contrast, this invention seeks to provide a more sensitive measurement to gauge performance properties such as % elongation at break.

Figure 2:
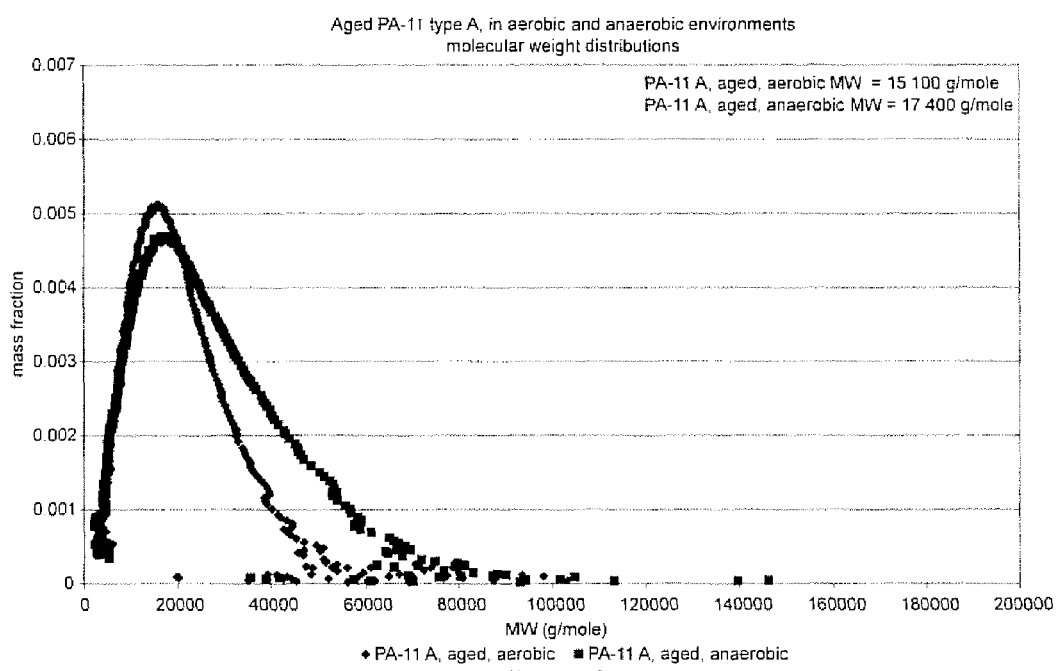
FIG. 2 shows a plot of molecular weight distributions of aerobic and anaerobic aged polyamide materials commonly used as the liner of a pipe.

In the practice of the invention, a detailed molecular weight distribution, molecular weight versus mass fraction of the polymer, is measured, as shown in FIGS. 1 and 2. Using this information, one can precisely determine a fraction of the polymer chains with a length greater than a critical molecular weight (a molecular weight value where chain entanglement becomes significant). This is a much more meaningful and accurate method for determining the tensile properties of the polymer material at any point during aging while in use.

Using the same methods to determine the chain lengths/molecular weight versus mass fraction of the polymer, one can determine the amount of material that exists as monomer. This can vary with age, type of chemical aging, as well as other factors. Methods involving an average molecular weight as measured by light scattering or viscosity, which do not account specifically for, for example, large or small amounts of monomer, lead to scatter and lack of precision.

By looking at the breadth of the molecular weight distribution as, for example, shown in FIG. 2, for hydrolysis aging in the presence versus absence of oxygen, the inventive method also can be used to detect the type of chemical aging which is occurring. This is important as it is known in the literature that hydrolysis aging produces a final stable equilibrium chain length which if above the ductile brittle transition leads to a very long use life. But if oxygen is present, the reduction in chain lengths continues with time, there is no equilibrium. Being able to detect oxygen aging or the absence of oxidation is important in predicting the use life from periodic measurements of witness coupons over time, as well, as for example, allowing an operator to make changes in operations so as to reduce oxidation aging of pipe liners (e.g., drilling and oil and gas production may be varied to eliminate or reduce oxidative exposure to the pipe liner; similar corrective steps can be employed in other applications). Notably, in FIG. 2, the shape of the molecular weight distribution curve for the aerobically aged polymer is different from the anaerobically aged polymer (i.e., it has a sharper, less distributed shape). FIG. 2 demonstrates that the shape of the curve can be used by an operator or a computer to differentiate the types of aging occurring for various polymeric parts.

Figure 3:
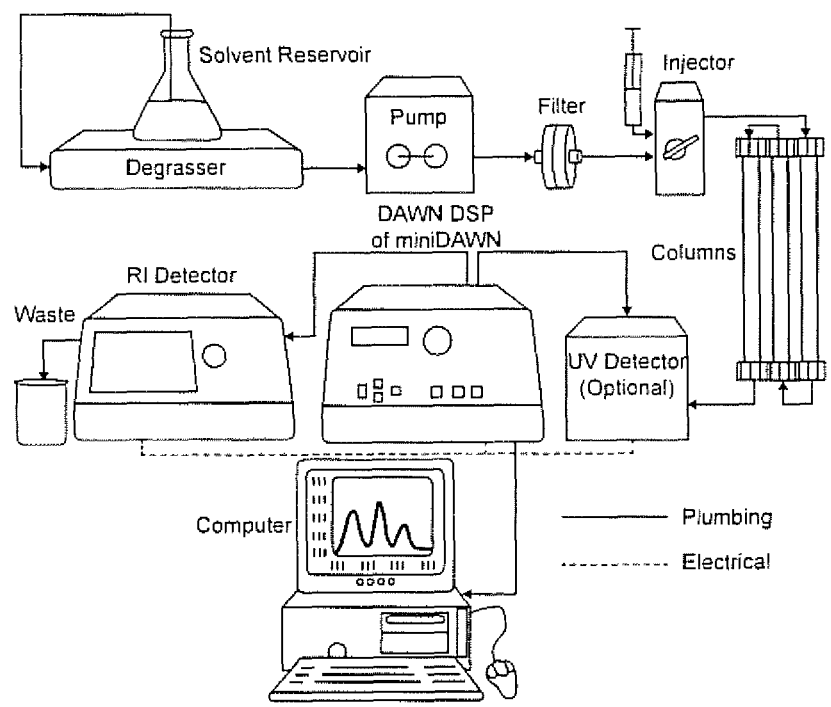
FIG. 3 shows an exemplary system for monitoring aging of polymeric materials.

An exemplary apparatus or system for measurement of the molecular weight distribution is shown in FIG. 3. All the components depicted are commercially available equipment. The equipment and various methods for detecting molecular weight of the fractionated fluid coming though the size exclusion columns such as by light scattering or viscometry and detecting the mass of the polymer at that time such as by refractive index or uv/visible absorption are well known and described in the literature. In short, in an exemplary system, polymeric material may be separated into individual chains using a solvent, and the individual chains may be separated by size (chain length which correlates with weight) using size exclusion columns (or by other suitable means), and the size of each of these chains may be measured using refractive index techniques, UV/Vis absorption, or by combinations of the two, or by other means. These molecular weights can be collected and analyzed using a computer which can record the distribution of the weights from the sample. As shown in FIGS. 1 and 2, the mass fraction of the polymers can be recorded so that, for example, one can see from a distribution plot (or table) the percentage of chains in the sample having specific weights. As demonstrated in FIG. 2, the shape of the molecular weight distribution curve is readily identified as different when comparing, for example aerobically aged PA-11 and anaerobically aged PA-11. The computer might be used to provide a prediction when a part needs to be replaced and it can send this information remotely to a production and/or ordering facility so as to achieve timely replacement. The computer might also be set up to provide alerts (audio or visual alarms) to provide replacement notifications, and/or to provide an operator with an alert that, for example, the aging which is occurring is oxidative as opposed to hydrolysis aging so that the operator can adjust the oil and gas production parameters to eliminate or reduce the oxidative aging.

Figure 4:
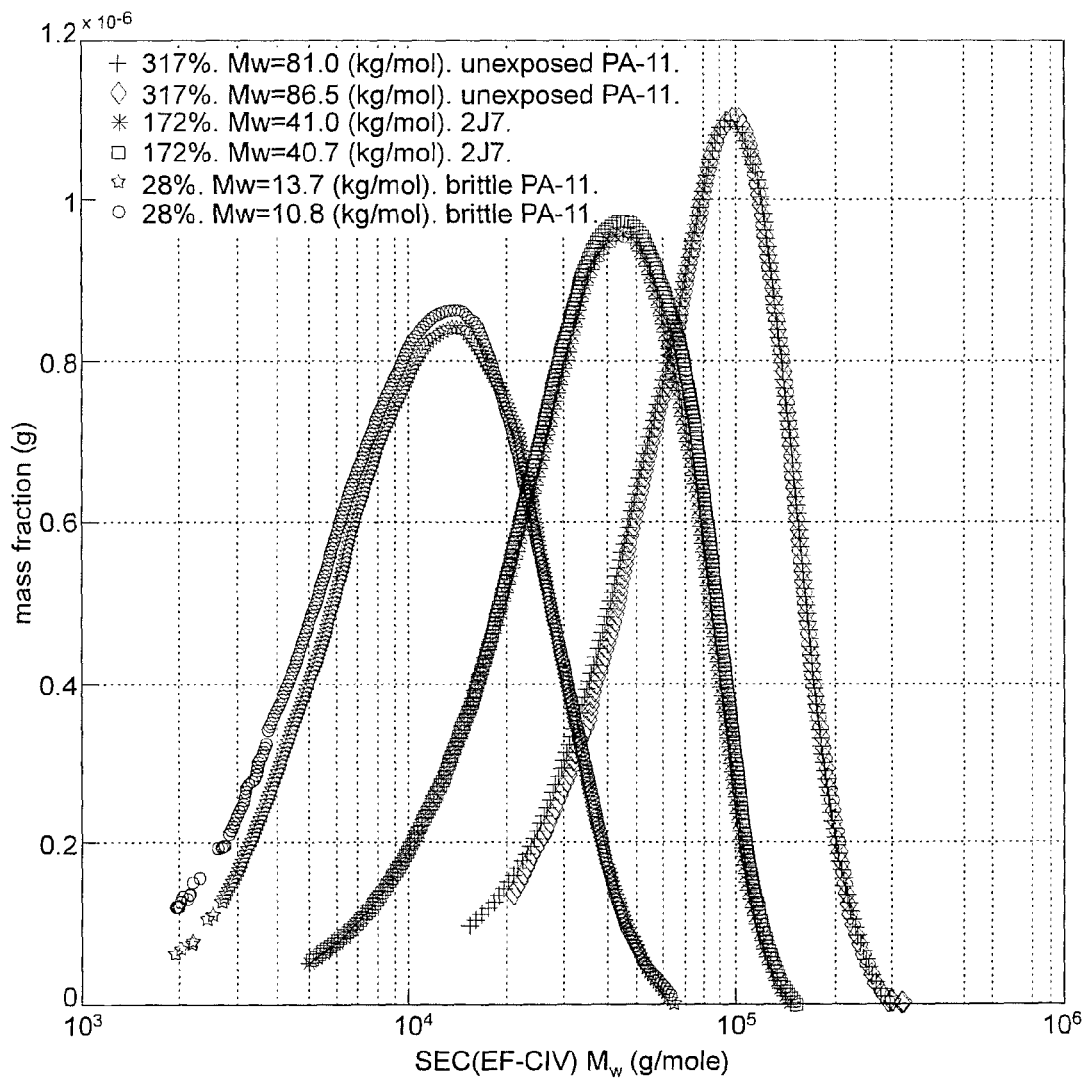
FIG. 4 shows molecular weight distribution plots of unaged, aged in the field, and aged to the point of brittleness witness coupons.
Figure 5:
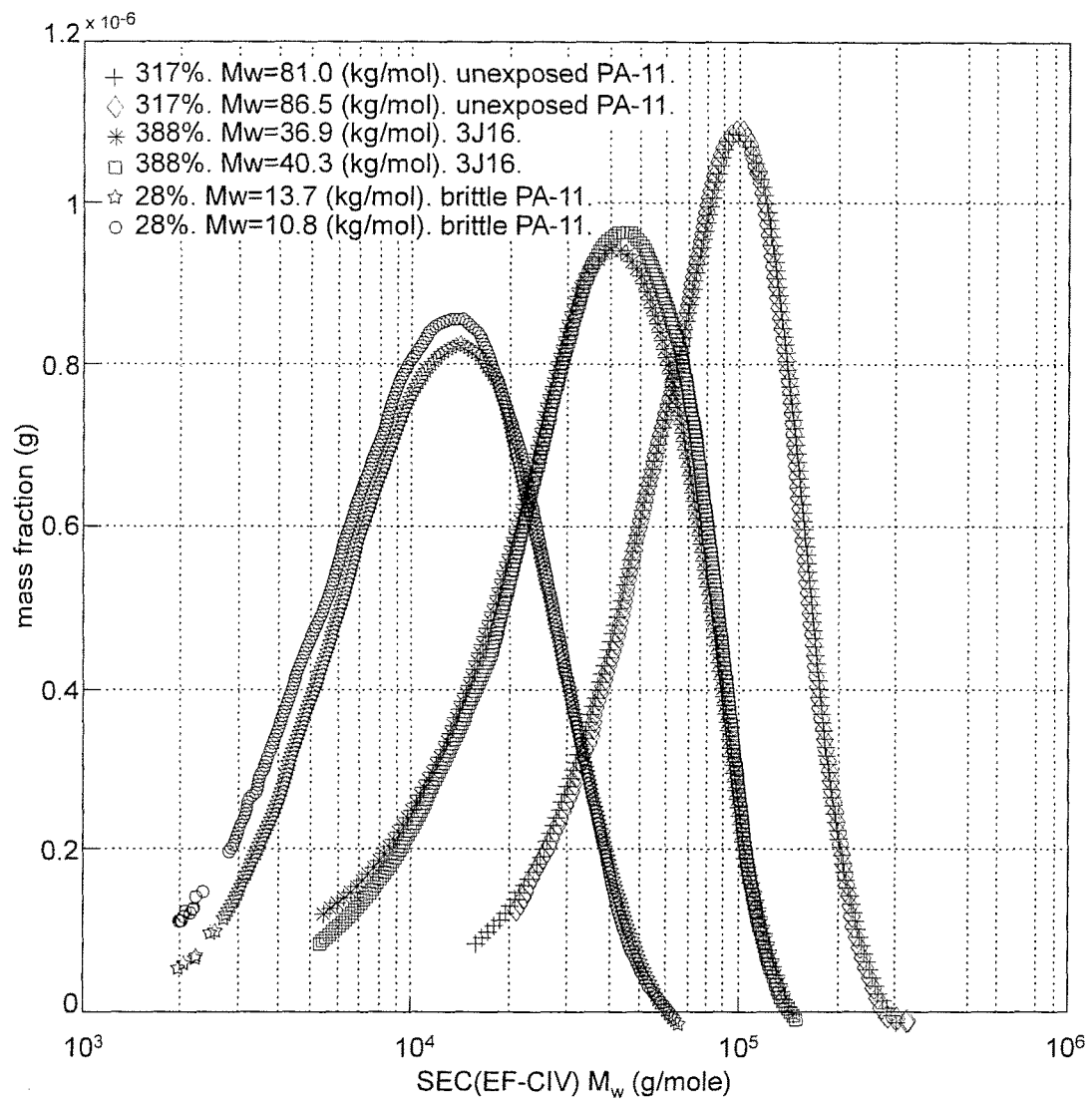
FIG. 5 shows molecular weight distribution plots of unaged, aged in the field, and aged to the point of brittleness witness coupons.
Figure 6:
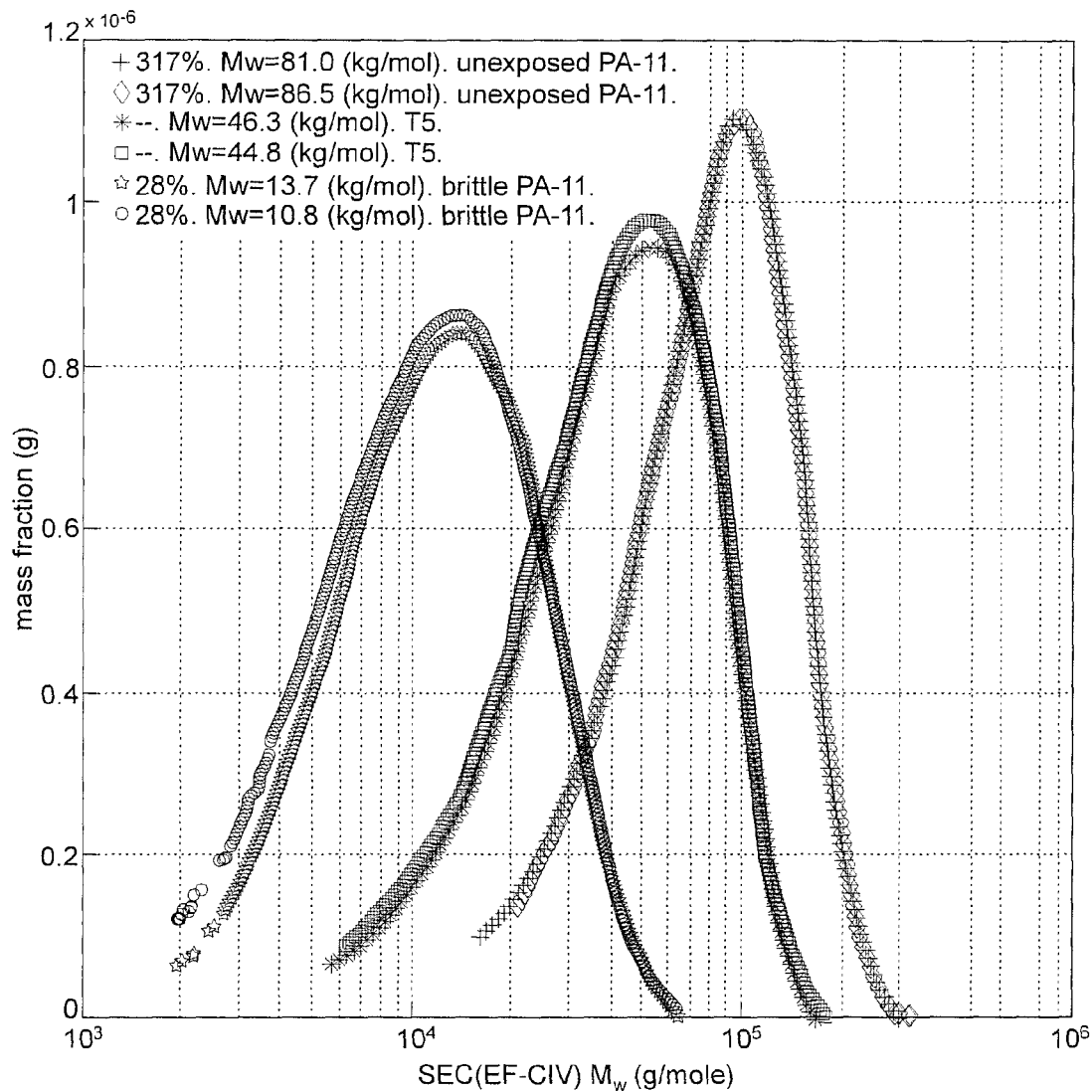
FIG. 6 shows molecular weight distribution plots of unaged, aged in the field, and aged to the point of brittleness witness coupons.

FIGS. 4-6 illustrate an exemplary use of the inventive technique to monitor the mechanical performance properties of a PA-11 liner (a polyamide formed from 11 aminoundecaonic acid) in a flexible pipe which is transporting a crude water mixture from the ocean floor to a floating platform. As discussed in U.S. Pat. No. 7,069,772 and U.S. Pat. No. 7,487,666, PA-11 witness coupons are inserted in the crude flowstream of the pipe throughout use. The witness PA-11 coupons are periodically removed and used to monitor the tensile elasticity of the flexible pipe's PA-11 liner, the maintenance of industry defined safety margins, and the extent of aging. In all three Figures (FIGS. 4-6), the PA-11 sample on the right is fresh, un-aged PA-11, and the sample on the left has degraded to a point where it is brittle and its % elongation at break falls below a recommended 50% value for safe continued use. The PA-11 samples in the middle are the molecular weight distribution for witness PA-11 coupon removed from a flexible PA-11 pipe during its years of service in the field.

FIG. 4 displays the distribution of the mass fraction of each chain length for duplicate runs on three samples. From FIG. 4 it is clear that as the PA-11 is exposed to the crude flowstream environment over time at a given temperature, the lengths of the chains becomes shorter. The most prominent chain length based on the mass contribution in the PA-11 sample shifts from about 100,000 grams/mole for the unexposed PA-11, to about 40,000-45,000 grams/mole for the moderately aged sample, to about 15,000 grams/mole for the most aged sample. At the same time, the elasticity as measured by % elongation at break shifts from over 317%, to 170% and then to 28% for the most aged sample. The recommended safe margin of elasticity for PA-11 flexible pipes used to transport crude from the ocean floor to platforms is 50%. Hence the most aged PA-11 coupon sample indicates that the flexible pipe from which it was removed no longer has the recommended elasticity for a prudent margin of safety. Its vulnerability to experience a break is too high. This sample of PA-11 is in the ductile brittle transition. FIG. 4 shows why. The distribution in the chain lengths is such that too large a fraction of the chains are short and can not experience the conformational changes which are needed to create elasticity. An example of how chain length creates elasticity is to realize that candle wax has no elasticity, the carbon chains are quite short, while polyethylene bottles are elastic as the carbon chains are much longer. The distribution presented in FIG. 4 clearly shows the extent of change in the chain lengths. The distribution plot of FIG. 4 can be used to monitor the true molecular basis for the chain's elasticity (although this same information can be evaluated in tables, and by other means). The average of the chain lengths, the weight average molecular weight, Mw, may track the aging process if the functional form of the distribution remains constant. As shown in FIG. 2 with changing aging processes, the function describing the distribution in chain lengths changes. Hence, Mw, the average of the chain lengths, does not provide the most accurate measure of aging and changes in performance properties; rather, the inventive process of having a multi-point molecular weight distribution determination provides a superior representation of aging and changes in performance properties.

FIG. 5 displays the molecular weight distribution of the chain lengths as measured by the individual polymer chains' molecular weights for a second witness coupon retrieved after years of exposure in the flow stream of a PA-11 lined flexible pipe. Here one observes the % elongation at break is even higher than a measurement on a fresh un-aged PA-11 coupon. This is because the % elongation measurements are not precise and requires at least three measurements on the same sample to achieve a reasonable precision. Furthermore, the tensile properties vary little as the chains become shorter until the chain lengths are near the values associated with the ductile brittle transition. At that point, % elongation drops quickly from above 300% to values below 50%. Hence measurements of the change in tensile properties are not able to monitor the aging process. Here in FIG. 5, one sees a like new % elongation at break, yet the PA-11 has aged a lot when one observes the distribution in the PA-11 sample's chain lengths as measured by each chain's mass, molecular weight. FIG. 5 shows that the mass distribution in the PA-11 coupons chain lengths has changed significantly. At this time, the 3J16 PA-11 coupon's chain lengths are about midway between the un-aged PA-11 and the distribution which exists when an aging polymer is brittle and no longer meets a recommended safety margin of 50% elongation at break.

FIG. 6 displays another comparison plot for which there are no tensile measurements. Yet the distribution in chain lengths shows that this coupon has aged but retains chain lengths well above that of PA-11 which is no longer fit for use with elasticity below 50% at break. Hence very small mg quantities of PA-11 used to measure the molecular weight distribution provide much more accurate and precise knowledge that this PA-11 material having aged in the flow-line retains tensile properties in the range of un-aged PA-11.

Further, FIGS. 4-6 show that a measurement of the mass fraction of the chains above a designated chain length determined from brittle aged chains with tensile % elongation properties below the recommended value of 50% can be used to monitor the extent of aging. For example, based on FIG. 6, the mass fraction of the chains above a reference length of Mw=20,000 grams/mole can be calculated for the un-aged PA-11 material and for the brittle PA-11 material with a % elongation just below the recommended safety factor of 50% elongation at break. The un-aged PA-11 has virtually all of its chains with a length greater than 20,000 grams/mole. The brittle PA-11 with a % elongation of 48% has only 23% of its mass composed of chains with a length greater than 20,000 grams/mole. The retrieved T5% PA-11 coupon has 82% of the mass of the sample composed of chains with a length greater than 20,000 grams/mole. The coupons 2J7 and 3J16 also have about 80% of their chains above this reference value of 20,000 grams/mole. Hence all three coupons have excellent tensile elongation at break properties. Clearly other reference values such as 15,000 grams/mole or 30,000 grams/mole could be used to determine the fraction of the chains above the reference value in a similar analysis comparing distributions to that of an unacceptable aged state. For example, 17,000 grams/mole or greater would be a good threshold value for polyamides formed from 11-aminoundecanoic acid which are used in flexible pipe liner applications, and having 25% or more of the chains greater than this threshold value would be preferable (that is, for a threshold for meeting a defined performance property of 50% elongation at break, at least 25% of the chains in the molecular weight distribution for the polymer should have a molecular mass greater than 17,000 grams/mole). However, it should be recognized that the threshold value and the percentage value can vary depending on the application and on the polymer employed—the invention contemplates that these values will be preset for each application. Further, other mechanical properties or other types of performance properties that arise from chain lengths being above a critical value can be monitored through chain length distribution measurements.

A plot of the fraction of the chains above the reference value for a series of coupons retrieved at varying times can be plotted versus time. From such a plot, the time at which the fraction of chains will approach that of brittle PA-11, or unacceptable properties can be estimated. For example, an operator can determine an estimate of the remaining use time for that PA-11 structure while maintaining the recommended performance property, such as % elongation at break.

Figure 7:
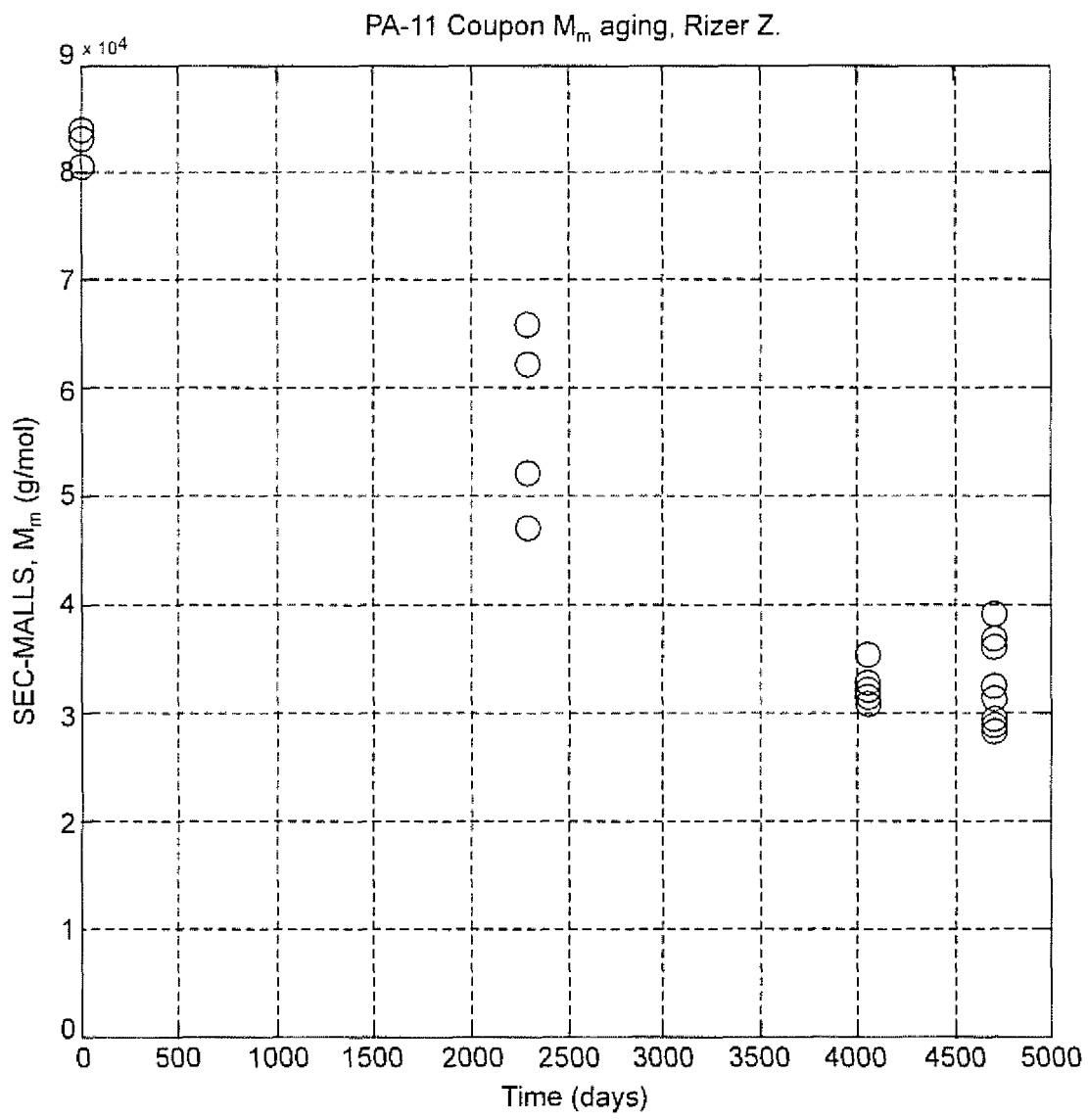
FIG. 7 is a graph showing the $M_m$ aging over time for riser coupons.

FIG. 7 shows the results of molecular weight measurements made over the years of operation on periodically retrieved witness coupons from the flow line of a polyamide flexible pipe used to transport crude in an offshore environment since installation over the past fourteen years. Here measurements on a coupon of the size as shown in FIG. 8 make it possible to perform multiple measurements on the surface and at varying depths to assess the extent of a gradient in the aging of the polymer.

Figure 8:
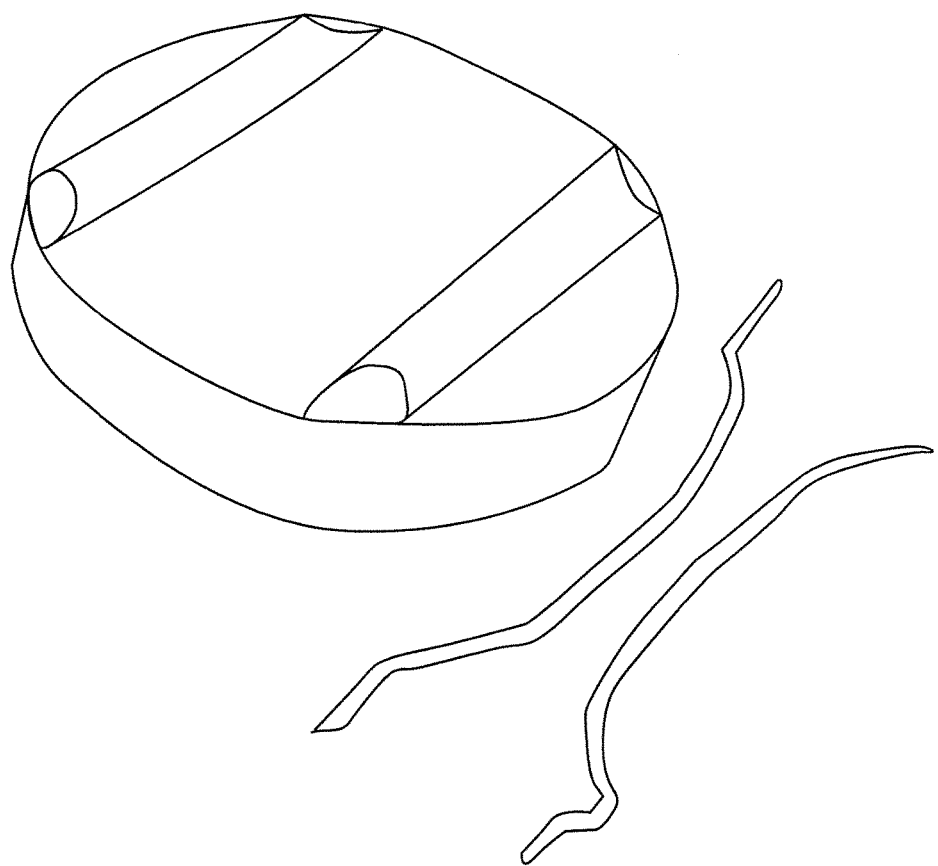
FIG. 8 is an exemplary riser coupon used to monitor the state of the pipe's polymer liner.

FIG. 8 is a witness coupon retrieved from the interior of a polyamide flexible off shore pipe after continuous exposure to the crude oil water mixture flowing through the pipe. The coupon was cut as a disk from a portion of the extruded polyamide liner during fabrication of the pipe. Witness coupons made from pre-aged polymer can also be used as they will show the aging properties of the pipe's polymer liner during the much later stages of use (as discussed in U.S. Pat. No. 7,069,772, and U.S. Pat. No. 7,487,666). Pre-aged coupons can be used to predict the existence and value of an equilibrium molecular weight far sooner than its actual occurrence. The witness coupon in FIG. 8 is 27 mm in diameter and 5.5 mm thick. Witness coupons of any size and specimens taken from the pipe's polymer liner down to a volume of 10 ml provide sufficient polymer material for the molecular weight-distribution measurement.

The invention claimed is:

1. A method for monitoring aging of polymer parts, comprising the steps of:
    distributing one or more witness coupons to one or more different locations adjacent to a polymer part whereby said witness coupons are exposed to identical in use conditions as said polymer part, and wherein said witness coupons are made of a polymer which is identical to said polymer part;
    periodically retrieving said one or more witness coupons;
    for each witness coupon retrieved, determining a molecular weight distribution for polymer chains in said witness coupon, said molecular weight distribution indicating a percentage of polymer chains that are longer than a critical length; and
    comparing a first molecular weight distribution and its percentage of polymer chains that are longer than the critical length determined at a first time point with a second molecular weight distribution and its percentage of polymer chains that are longer than the critical length determined at one or more successive time intervals; and
    determining one or more aging characteristics of said polymer part based on a comparison made in said comparing step, wherein said one or more aging characteristics are selected from the group consisting of
    a prediction of a useful life remaining for said polymer part, and
    a prediction that aging of said polymer part is caused by oxidation.

2. The method of claim 1 wherein said polymer part is made from a polymer selected from the group consisting of polyamide formed from 11-aminoundecanoic acid or 12-aminododecanoic acid, polyvinyldiflouride, and polyethyelene.

3. The method of claim 1 wherein the polymer sample is a vinyl addition polymer.

4. The method of claim 3 wherein said vinyl addition polymer is selected from the group consisting of polystyrene, polypropylene, polyvinylchloride, polyvinyldifluoride, and polyethylene.

5. The method of claim 1 wherein said polymer sample is a polyamide or a polyester.

* * * * *